United States Patent
Kang et al.

(10) Patent No.: US 8,512,611 B2
(45) Date of Patent: Aug. 20, 2013

(54) MANUFACTURING METHOD OF TOOTHBRUSH FILAMENTS USING POWER TOOTHBRUSH AND TOOTHBRUSH USING THEREOF

(75) Inventors: Yeon-Bok Kang, Daejeon (KR); Ki-Tae Kang, Daejeon (KR); Gui-Hwan Oh, Daejeon (KR)

(73) Assignee: BBC Co., Ltd., Daejeon (KR)

( * ) Notice: Subject to any disclaimer, the term of this patent is extended or adjusted under 35 U.S.C. 154(b) by 280 days.

(21) Appl. No.: 12/870,299

(22) Filed: Aug. 27, 2010

(65) Prior Publication Data

US 2011/0289701 A1    Dec. 1, 2011

(30) Foreign Application Priority Data

May 31, 2010  (KR) .................. 10-2010-0050954

(51) Int. Cl.
*A46D 1/04*   (2006.01)
(52) U.S. Cl.
USPC ........................................... 264/148
(58) Field of Classification Search
CPC .......... A46D 1/0276; A46D 1/04; A46D 1/05
USPC ........................................ 15/207.2; 264/148
See application file for complete search history.

(56) References Cited

U.S. PATENT DOCUMENTS

| | | | | |
|---|---|---|---|---|
| 6,048,478 | A * | 4/2000 | Weihrauch | 264/103 |
| 6,090,488 | A | 7/2000 | Kweon | |
| 6,199,242 | B1 * | 3/2001 | Masterman et al. | 15/167.1 |
| 8,167,379 | B1 * | 5/2012 | Lee | 300/21 |

FOREIGN PATENT DOCUMENTS

| | | |
|---|---|---|
| DE | 69315805 T2 | 6/1998 |
| DE | 19838201 A1 | 9/1999 |
| JP | 6366943 A | 3/1988 |
| JP | 6141923 A | 5/1994 |
| JP | 2004202065 A | 7/2004 |
| JP | 2008154888 A | 7/2008 |
| WO | 2006107123 A1 | 10/2006 |

* cited by examiner

*Primary Examiner* — Yogendra Gupta
*Assistant Examiner* — Alison Hindenlang
(74) *Attorney, Agent, or Firm* — The Webb Law Firm

(57) ABSTRACT

Provided is a tapered filament for a power toothbrush made of a synthetic resin and formed with tapers at two ends thereof and a non-tapered area for tufting part of which middle is tufted into a power toothbrush, wherein an overall length is 16 to 22 mm, a length of the non-tapered area for tufting part is 4 to 12 mm, and the rest parts except for the non-tapered area for tufting part form tapers at two ends.

7 Claims, 2 Drawing Sheets

MANUFACTURING METHOD OF TOOTHBRUSH FILAMENTS USING POWER TOOTHBRUSH AND TOOTHBRUSH USING THEREOF

CROSS-REFERENCE(S) TO RELATED APPLICATIONS

The present invention claims priority of Korean Patent Application No. 10-2010-0050954, filed on May 31, 2010, which is incorporated herein by reference.

BACKGROUND OF THE INVENTION

1. Field of the Invention

The present invention relates to a double tapered filament for a power toothbrush and a method for manufacturing the same. More particularly, the present invention relates to a double tapered filament having excellent durability even with a short length so as to be suitable for the use in a power toothbrush, and a method for manufacturing the same.

2. Description of Related Art

A filament for a toothbrush, which is first made of nylon, has been significantly changed with development of various tapered filaments using polybutylene terephthalate (PBT). Current tapered filament is increasingly demanded by many people since the filament has solved the problems of existing filament made of nylon, such as bending and sanitation, and has excellent accessibility to a periodontal pocket. In addition, various toothbrushes having a functional filament or changed tufting form, which is beyond the established viewpoints, have been introduced, and new types of high-grade toothbrushes using electric power or ultrasonic wave have also been developed.

However, the filament used in a power toothbrush has two important features. First, the filament is required to maintain its stiffness or strength in a toothbrush rotating at high speed; and second, a part of a brush head connected with a power part has a predetermined thickness and thus a tufting length of a brush part except for the connection part should have a quite shorter length than that of a manual toothbrush (general toothbrush). That is, since a tuft part of the power toothbrush has a thickness greater than that of a manual toothbrush, the length of the filament of the power toothbrush should have a relatively short length in order to control an overall height of the toothbrush.

Particularly, unlike the general filament which is tufted into the brush head in a "V" shape and then cut to a predetermined length, in the case of the tapered filament, the tapered filament is previously manufactured so as to have two tapered ends and then tufted into the brush head. Therefore, to tuft this tapered filament into the power toothbrush, it is important for the tapered filament to maintain its short overall length as well as have a short taper with a uniform shape.

SUMMARY OF THE INVENTION

An embodiment of the present invention is directed to providing a method for manufacturing a tapered filament which is able to be tufted to a power toothbrush and has excellent durability upon high speed rotation.

Another embodiment of the present invention is directed to providing a method for manufacturing a tapered filament, which has a tapered shape and is manufactured in a short length so as to ensure a predetermined tufting area, and thus prevents an overall thickness of a brush head from being thickened by a thick power part.

To achieve the object of the present invention, the present invention provides a double tapered filament for a power toothbrush and a method for manufacturing the same. Particularly, the present invention provides a tapered filament, which has not only a short overall length but also two short tapered ends to allow proper control of a length of the non-tapered area for tufting part to be tufted, so that the filament can be used in a power toothbrush.

Specifically, the present invention provides a double tapered filament for a power toothbrush made of a synthetic resin and formed with tapers at two ends thereof and a tufting part of which middle is tufted into a power toothbrush, wherein an overall length is 16 to 22 mm, a length of the non-tapered area for tufting part is 4 to 12 mm, and the rest parts except for the non-tapered area for tufting part form tapers at two ends.

In the double tapered filament for a power toothbrush, a diameter (thickness) at 0 to 1 mm from an end point is 0 to 45% of a central diameter of a filament (thickness at half position of overall length of the filament), a diameter at 1 to 3 mm from the end point is 35 to 85% of the central diameter of the filament and a diameter at 3 to 6 mm from the end point is 60 to 97% of the central diameter of the filament.

The diameter at each portion is calculated using the following equation 1.

$$\text{Diameter ratio} = (\text{Central diameter of each portion}/\text{Central diameter at half position of the filament}) \times 100 \quad [\text{Equation 1}]$$

Also, the present invention provides a method for manufacturing a tapered filament for a power toothbrush, which includes:

a) melt spinning a synthetic resin composition and then stretching the spun product to 4 to 6 times to manufacture a monofilament with a diameter of 0.1 to 0.25 mm;

b) processing the monofilament into a bundle with a diameter of 40 to 55 mm;

c) cutting the bundle to a length of 105 to 115% of a length of the final product;

d) heating an end of the bundle to a melting temperature of the synthetic resin to melt a portion of 1 to 3 mm;

e) dipping an end opposite to the melted end in a processing bath containing an alkali solution at 100 to 140° C. and 30 to 60% concentration to taper the opposite end; and f) dipping the melted end in a processing bath containing an alkali solution at 100 to 140° C. and 30 to 60% concentration to taper the melted end.

Hereinafter, the present invention will be described in more detail.

The present invention provides a double tapered filament made of a synthetic resin and formed with tapers at two ends thereof and a non-tapered area for tufting part of which middle is tufted into a power toothbrush, wherein an overall length is 16 to 22 mm, a length of the non-tapered area for tufting part is 4 to 12 mm, and the rest parts except for the non-tapered area for tufting part form tapers at two ends. When the aforementioned condition is satisfied, a height H1 of the tapered filament 40 from a tufting surface 30 of a toothbrush after tufted to the power toothbrush is 5 to 8.5 mm and this is suitable for use.

It is also preferred for convenience use that an overall height H2 of a toothbrush head 100 including the length of the tufted tapered filament 40 is 14 to 19 mm. (see FIG. 4).

Particularly, the present invention is characterized in that the tapered filament is formed with tapers at two ends thereof while formed with a short overall length of 16 to 22 mm so that it can be employed in a power toothbrush, and is also characterized by a method for manufacturing the tapered filament. Conventionally, a non-tapered area for tufting part of 4 to 12 mm length is required for tufting to a power toothbrush: if less than 4 mm, the length of the non-tapered area for tufting part is short and it is highly possible for the tapered filament to be deviated when tufted into the brush part in a tufting machine, and if more than 12 mm, it is not preferred that the tapered part may not be completely tapered.

In general, a filament for a power toothbrush has an overall length of 16 to 22 mm, which is very short than that of a general filament. This is because a power part is mounted in a brush head onto which the filament is tufted and thus the brush head is thicker than that of a manual toothbrush. Therefore, when processing the monofilament into a bundle and dipping the bundle in an alkali solution so as to form taper parts at two ends thereof, since the alkali solution moves up along between the filaments by the capillary action even though a minimum length of the end is dipped in the alkali solution, almost no non-tapered area for tufting part except for the taper part is formed at two ends (see FIGS. 2 and 3). Consequently, it was impossible to manufacture a double tapered filament for a power toothbrush.

The present inventors have studied for manufacture of a double tapered filament capable of being tufted into a power toothbrush, and as the result, have completed the present invention from the discovery that it is possible to taper the filament by a desired length by way of heating to melt close an end of a bundle of monofilaments, so that the alkali solution cannot move up along between the monofilaments by the capillary action, after melt spinning a synthetic resin composition to manufacture the monofilaments and processing the monofilaments into a bundle so that it can be easily tapered.

That is, the present invention is characterized by a process for manufacturing a double tapered filament, and this manufacturing method includes the steps of melt spinning a synthetic resin composition, processing stretched monofilaments into a bundle, melt closing an end of the bundle by heating the end to the melting temperature of the synthetic resin, and dipping the opposite end in a processing bath containing an alkali solution to taper the opposite end.

More specifically, the method includes:

a) melt spinning a synthetic resin composition and then stretching the spun product to 4 to 6 times to manufacture a monofilament with a diameter of 0.1 to 0.25 mm;

b) processing the monofilaments into a bundle with a diameter of 40 to 55 mm;

c) cutting bundle to a length of 105 to 115% of a length of a final product;

d) heating an end of the bundle to a melting temperature of the synthetic resin to melt close the portion exceeding 1 to 3 mm of the length;

e) dipping an end opposite to the melted end in a processing bath containing an alkali solution at 100 to 140° C. and 30 to 60% concentration to taper the opposite end; and f) dipping the melted end in a processing bath containing an alkali solution at 100 to 140° C. and 30 to 60% concentration to taper the melted end.

Also, if necessary, the method may further include cleaning the portion in the taper where the alkali solution and the resin react to lump together after the step e) and the step f), respectively.

In the present invention, the synthetic resin composition is a mixture of polyester resin and an additive. At this time, a usable additive includes calcium carbonate, silica, nano-silver powder, nano-platinum powder, charcoal powder, $TiO_2$, TiON, fluorine and antibiotic. Also, the polyester resin includes one or a mixture of two or more selected from the group consisting of polyethylene terephthalate (PET), polytrimethylene terephthalate (PTT) and polybutylene terephthalate (PBT). It is preferred for enhanced durability upon high speed rotation that the synthetic resin has a tensile strength of 250 to 2500 cN and an elongation of 15 to 30%.

In the melt spinning, the aforementioned mixture of the additive and the synthetic resin is extruded using an extruder heated to 220 to 280° C. with a nozzle having plurality of holes (4 to 120) having a diameter of 0.2 to 2 mm, stretched at a stretch ratio of 4 to 6 times, and then wound on a winder. At this time, it is preferred for manufacture of a filament with excellent durability that the stretch is implemented four times and the temperature of the each stretcher is in a range of 150 to 220° C.

The stretch is preferably implemented to 4 to 6 times: if less than 4 times, color change is generated, strength is weak and the elongation is raised, and if more than 6 times, flexibility is notably low and cut off is generated during the stretch.

It is preferred that a diameter of the monofilament manufactured after the stretch is 0.1 to 0.25 mm. If less than 0.1 mm, the filament is too thin and thus easily bent and has notably low cleaning ability, and more than 0.25 mm, the filament has good cleaning ability but the toothbrush is too strong to affect restoring force and lower brushing feeling.

Next, a bundle is manufactured by cutting the manufactured monofilaments to a predetermined length, and the length is preferably 105 to 115% of the length of the final product (for example, 16.8 to 18.4 mm if the length of the final product is 16 mm). This is because in this range, an error of the portion tapered and lost when dipped in the alkali solution can be reduced. A diameter of the bundle is preferably 40 to 55 mm for easy arrangement of the tapered filament after manufacture and suitable use in the tufting machine.

Next, an end of the bundle is heated to the melting temperature of the synthetic resin to melt close the portion at 1 to 3 mm from the end, thereby capable of preventing the capillary action.

After that, an end opposite to the melted portion is dipped in a processing bath containing an alkali solution at 100 to 140° C. and 30 to 60% concentration to thereby be tapered.

Also, the alkali solution may employ sodium hydroxide of 30 to 60% concentration, and is preferably heated to a temperature of 100 to 140° C. for reduced tapering time and obtainment of stable tapered filament. At this time, it is preferred that a temperature deviation in the processing bath is ±2° C. If the temperature deviation is out of this range, there are difference in the length and difference in the tapered shape even in the bundle processed in the same processing bath. Therefore the temperature deviation should not be out of this range. In this process, the resin in the tapered portion is hydrolyzed and the tapered and decomposed resin is lumped together with the alkali, so that the opposite end is closed like the resin in the melted state resin.

Upon the tapering, the non-tapered area for tufting part except for the taper part is formed to a length of 4 to 12 mm so as to enable the tufting. To this end, it is preferred that the dipping is implemented only to the point at 4 mm or less from the end point. If the dipping is implemented to the point at 4 mm or less from the end point, the alkali solution is not permeate further in the state that the opposite melt closed portion under an atmospheric pressure, and a taper part having a length of 3 to 6 mm can be formed.

Next, the end of the melt closed portion is dipped in a processing bath containing an alkali solution at 100 to 140° C. and 30 to 60% concentration to thereby be tapered through the process as described above. In this process, the tapered portion is hydrolyzed and a lumped portion is formed again in the end of the melt closed portion.

Next, the hydrolyzed portions are cleaned and removed to form the taper parts. At this time, the cleaning is implemented with flowing water, and finally the alkali is neutralized using dilute sulfuric acid and cleaning with water is implemented again.

In the present invention, the taper part is preferably manufactured so that a diameter at 0 to 1 mm from an end point is 0 to 45% of a central diameter at half position of the filament, a diameter at 1 to 3 mm from the end point is 35 to 85% of the central diameter at half position of the filament and a diameter at 3 to 6 mm from the end point is 60 to 97% of the central diameter at half position of the filament. The tapered filament made in this range has a tapered shape, i.e. a shape having a length of the non-tapered area for tufting part of at least 4 mm and an overall length of 16 to 22 mm, that is impossible to be manufactured by a conventional method, and is the tapered filament that can be tufted into a power toothbrush and has a strength stable to a high speed rotation force and excellent brushing feeling.

The double tapered filament manufactured according to the method as described above has such a shape that an overall length of a final product is 16 to 22 mm, a length of the non-tapered area for tufting part is 4 to 12 mm, and the rest parts except for the non-tapered area for tufting part form tapers.

A power toothbrush employing the double tapered filament manufactured by the method as described above is also included in the scope of the present invention. Further, a power toothbrush in which a height H1 of the tapered filament from a tufting surface 30 of a power toothbrush after tufted into the power toothbrush is 5 to 8.5 mm is also included in the scope of the present invention. (see FIG. 4)

Hereinafter, the double tapered filament for a power toothbrush will be described with reference to accompanying drawings.

FIG. 1 illustrates a double tapered filament in accordance with the present invention, in which sufficient spaces are ensured in the left and right sides of a half position $C_L$ of the filament and this enables stable tufting since taper parts 20a, 20b of the same length are formed in both ends of the filament, and the half position $C_L$ of the filament to be tufted to a tufting surface of a brush head is placed in the center of a tufting part 10.

FIG. 2 illustrates an example in that a monofilament is manufactured to a bundle and treated with an alkali solution without melt close, in which the tufting is impossible or the filament may be easily separated even though it is tufted since a non-tufted area Ls is placed out of the tufting part 10.

FIG. 3 illustrates another example in that a monofilament is manufactured to a bundle and treated with an alkali solution without melt close, in which the tufting is impossible since there is no non-tufted area Ls.

In the double tapered filament for a power toothbrush, a diameter at 0 to 1 mm from an end point is 0 to 45% of a central diameter of a filament, a diameter at 1 to 3 mm from the end point is 35 to 85% of the central diameter of the filament and a diameter at 3 to 6 mm from the end point is 60 to 97% of the central diameter of the filament.

It is preferred that the tapered filament for a power toothbrush has a diameter of 0.1 to 0.25 mm since the filament in this diameter range prevents easy bending and forms stable brushing feeling.

In the present invention, the synthetic resin is polyester, and specifically, may include one or mixture of two or more selected from the group consisting of polyethylene terephthalate (PET), polytrimethylene terephthalate (PTT) and polybutylene terephthalate (PBT). It is more preferred that the synthetic resin has a tensile strength of 250 to 2500 cN and an elongation of 15 to 30%.

Also, a conventional additive besides the synthetic resin used in the art may further be added if necessary. A usable additive includes calcium carbonate, silica, nano-silver powder, nano-platinum powder, charcoal powder, $TiO_2$, TiON, fluorine and antibiotic, and in addition a conventional additive may be further added if necessary.

In accordance with the present invention, it is possible to manufacture a tapered filament with high strength which has a short overall length and is formed with taper parts at two ends while ensuring a tufting part with a minimum length.

[Detailed Description of Main Elements]

Figure 1:
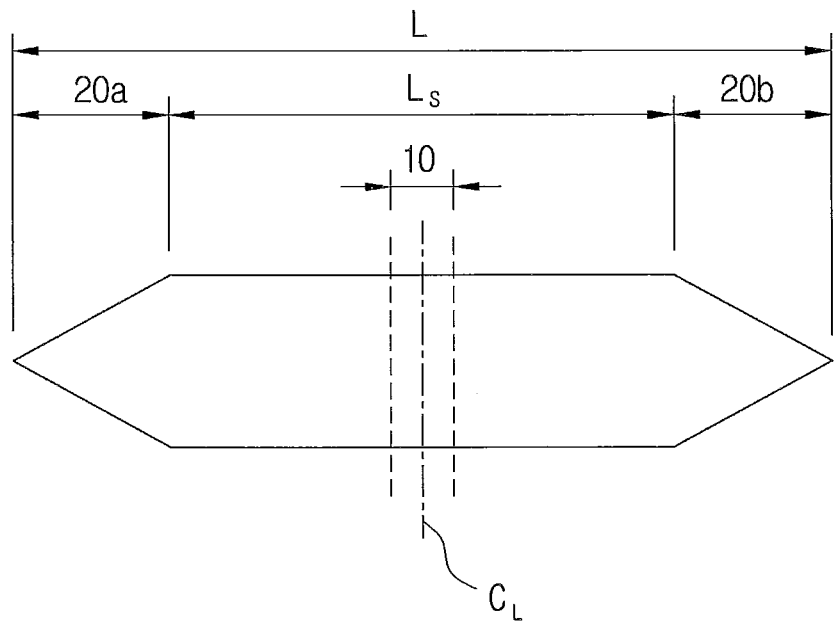
FIG. 1 illustrates an example of a double tapered filament manufactured in accordance with the present invention.
Figure 2:
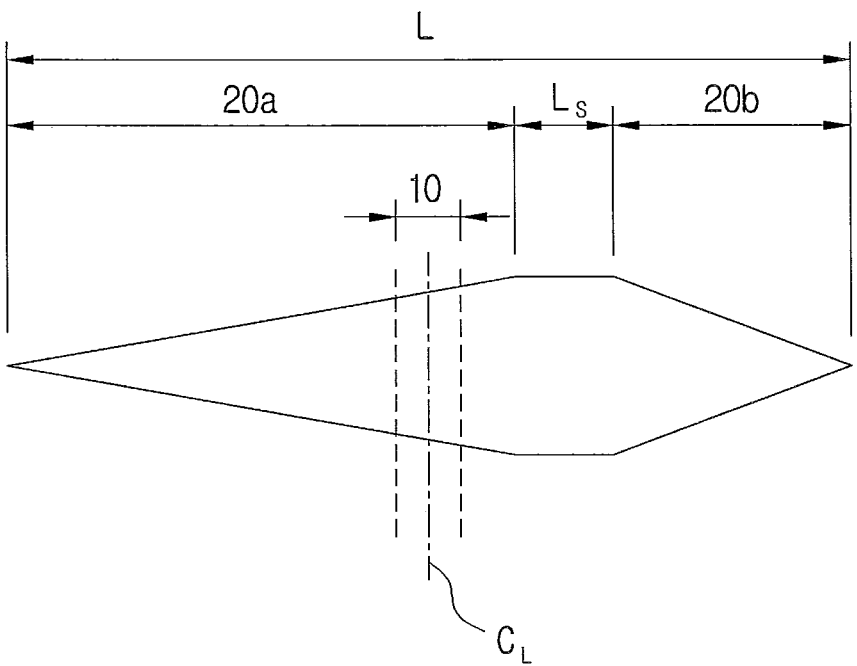
FIG. 2 illustrates an example of a double tapered filament manufactured by a conventional method.
Figure 3:
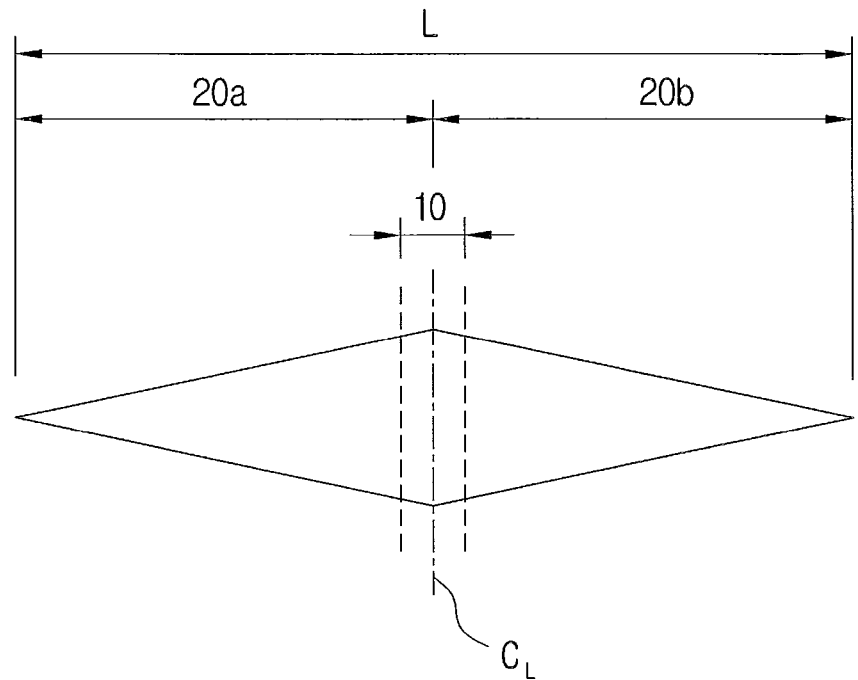
FIG. 3 illustrates another example of a double tapered filament manufactured by a conventional method.
Figure 4:
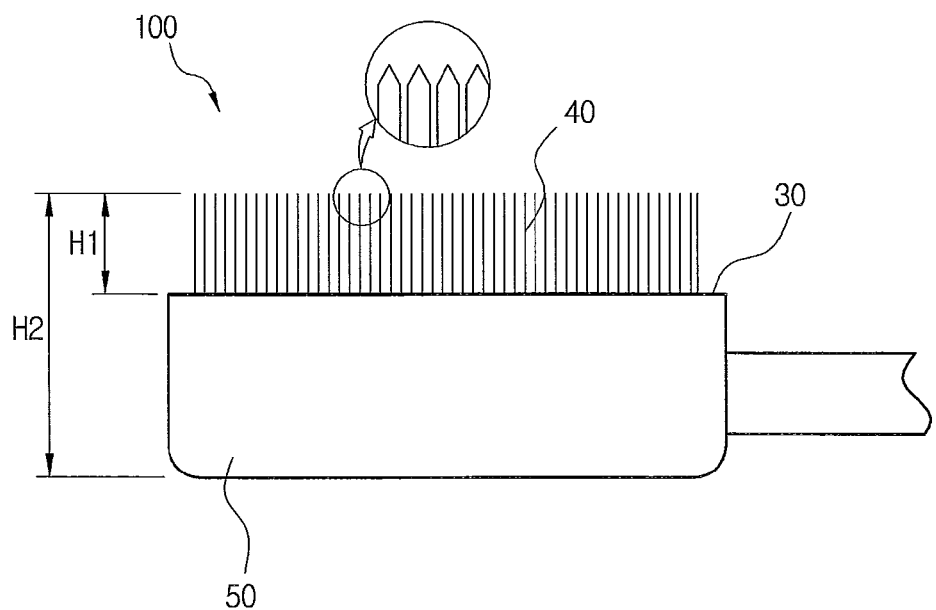
FIG. 4 illustrates an example of a tufting part of a power toothbrush using a double tapered filament according to a manufacturing method of the present invention

| | |
|---|---|
| L; | overall length |
| Ls: | non-tapered area for tufting part |
| $C_L$: | half position of the filament |
| 10: | tufting part |
| 20a, 20b: | taper part |
| 30: | tufting surface |
| 40: | tapered filament |
| 50: | power part |
| 100: | toothbrush head |
| H1: | height of the tapered filament |
| H2: | overall height of a toothbrush head |

DESCRIPTION OF SPECIFIC EMBODIMENTS

The advantages, features and aspects of the invention will become apparent from the following description of the embodiments with reference to the accompanying drawings, which is set forth hereinafter.

Example 1

Polybutylene terephthalate resin (Toraycon 1100, Toray) was put into an extruder and melt extruded at 250° C., followed by spinning using a nozzle with a size of 0.8 mm. The spun yarn was cooled with water and then stretched to 4 times, thereby manufacturing monofilament with a diameter of 0.2 mm.

The stretched monofilaments were bundled and cut, thereby manufacturing a bundle having a diameter of 40 mm and a height of 18.4 mm (corresponding to 115% of a length of the final product).

Heat of 250° C. was applied to an end of the manufactured bundle to melt close a portion at 1 mm from the end.

The side opposite to the melt closed side was dipped in a 35%, 110° C. aqueous sodium hydroxide solution for 180 minutes and then taken out. At that time, the dipping was implemented only to the portion at 4 mm from the end. White lump formed by hydrolysis of the resin was produced in the dipped portion.

Next, the melt closed portion was dipped in a 35%, 110° C. aqueous sodium hydroxide solution for 200 minutes and then taken out. At that time, the dipping was implemented only to the portion at 4 mm from the end. White lump formed by hydrolysis of the resin was produced in the dipped portion.

The white lumps produced in the two ends were cleaned two times with water, followed by neutralization using dilute sulfuric acid and cleaning with water.

As the result, a double tapered filament, which has an overall length of 16 mm, and is formed with a non-tapered area for tufting part with a length of 5 mm and taper parts with a length of 5.5 mm at two ends, was manufactured.

The taper part was inspected using a toolmaker's microscope (Olympus), and as the result, it was found that a diameter at 1 mm from an end point is 42% of a central diameter at half position of the filament, a diameter at 3 mm from the end point is 72% of the central diameter at half position of the filament and a diameter at 5.5 mm from the end point is 93% of the central diameter at half position of the filament.

Example 2

The same as Example 1 except that a mixture of polyethylene terephthalate (Samyang, Triloy) and polybutylene terephthalate resin (Toraycon 1100, Toray) in a weight ratio of 1:1 was used as a yarn material.

As the result, a double tapered filament, which has an overall length of 16 mm, and is formed with a tufting part with a length of 5 mm and taper parts with a length of 5.5 mm at two ends, was manufactured.

The taper part was inspected using a toolmaker's microscope (Olympus), and as the result, it was found that a diameter at 1 mm from an end point is 41% of a central diameter at half position of the filament, a diameter at 3 mm from the end point is 78% of the central diameter at half position of the filament and a diameter at 5.5 mm from the end point is 91% of the central diameter at half position of the filament.

Example 3

The same as Example 1 except that 5 parts by weight of calcium carbonate (mean particle size of 5 μm, Shinwon trading) was mixed for 100 parts by weight of polybutylene terephthalate resin (Toraycon 1100, Toray) and the mixture was used as a yarn material.

As the result, a double tapered filament, which has an overall length of 16 mm, and is formed with a non-tapered area for tufting part with a length of 5 mm and taper parts with a length of 5.5 mm at two ends, was manufactured.

The taper part was inspected using a toolmaker's microscope (Olympus), and as the result, it was found that of a diameter at 1 mm from an end point is 44% of a central diameter at half position of the filament, a diameter at 3 mm from the end point is 79% of the central diameter at half position of the filament and diameter at 5.5 mm from the end point is 92% of the central diameter at half position of the filament.

Example 4

The same as Example 1 except that 5 parts by weight of silica (mean particle size of 20 μm, Seonjin chemical) was mixed for 100 parts by weight of polybutylene terephthalate resin (Toraycon 1100, Toray) and the mixture was used as a yarn material.

As the result, a double tapered filament, which has an overall length of 16 mm, and is formed with a non-tapered area for tufting part with a length of 5 mm and taper parts with a length of 5.5 mm at two ends, was manufactured.

The taper part was inspected using a toolmaker's microscope (Olympus), and as the result, it was found that a diameter at 1 mm from an end point is 39% of a central diameter at half position of the filament, a diameter at 3 mm from the end point is 79% of the central diameter at half position of the filament and a diameter at 5.5 mm from the end point is 90% of the central diameter at half position of the filament.

Example 5

The same as Example 1 except that 0.1 parts by weight of nano-silver powder (mean particle size of 50 nm, ABC nanotech) was mixed for 100 parts by weight of polybutylene terephthalate resin (Toraycon 1100, Toray) and the mixture was used as a yarn material.

As the result, a double tapered filament, which has an overall length of 16 mm, and is formed with a non-tapered area for tufting part with a length of 5 mm and taper parts with a length of 5.5 mm at two ends, was manufactured.

The taper part was inspected using a toolmaker's microscope (Olympus), and as the result, it was found that a diameter at 1 mm from an end point is 40% of a central diameter at half position of the filament, a diameter at 3 mm from the end point is 81% of the central diameter at half position of the filament and a diameter at 5.5 mm from the end point is 94% of the central diameter at half position of the filament.

Example 6

The same as Example 1 except that 0.2 parts by weight of nano-platinum powder (mean particle size of 60 mm, ABC nanotech) was mixed for 100 parts by weight of polybutylene terephthalate resin (Toraycon 1100, Toray) and the mixture was used as a yarn material.

As the result, a double tapered filament, which has an overall length of 16 mm, and is formed with a non-tapered area for tufting part with a length of 5 mm and taper parts with a length of 5.5 mm at two ends, was manufactured.

The taper part was inspected using a toolmaker's microscope (Olympus), and as the result, it was found that a diameter at 1 mm from an end point is 41% of a central diameter at half position of the filament, a diameter at 3 mm from the end point is 77% of the central diameter at half position of the filament and a diameter at 5.5 mm from the end point is 91% of the central diameter at half position of the filament.

Example 7

The same as Example 1 except that 0.1 parts by weight of TiON (titanium oxynitride, Enbio) was mixed for 100 parts by weight of polybutylene terephthalate resin (Toraycon 1100, Toray) and the mixture was used as a yarn material.

As the result, a double tapered filament, which has an overall length of 16 mm, and is formed with a non-tapered area for tufting part with a length of 5 mm and taper parts with a length of 5.5 mm at two ends, was manufactured.

The taper part was inspected using a toolmaker's microscope (Olympus), and as the result, it was found that a diameter at 1 mm from an end point is 42% of a central diameter at half position of the filament, a diameter at 3 mm from the end point is 84% of the central diameter at half position of the filament and a diameter at 5.5 mm from the end point is 93% of the central diameter at half position of the filament.

Example 8

The same as Example 1 except that 0.5 part by weight of fluorine (NaF, Merk) was mixed for 100 parts by weight of polybutylene terephthalate resin (Toraycon 1100, Toray) and the mixture was used as a yarn material.

As the result, a double tapered filament, which has an overall length of 16 mm, and is formed with a non-tapered area for tufting part with a length of 5 mm and taper parts with a length of 5.5 mm at two ends, was manufactured.

The taper part was inspected using a toolmaker's microscope (Olympus), and as the result, it was found that a diameter at 1 mm from an end point is 42% of a central diameter at half position of the filament, a diameter at 3 mm from the end point is 78% of the central diameter at half position of the filament and a diameter at 5.5 mm from the end point is 90% of the central diameter at half position of the filament.

Example 9

Manufacture of a tapered filament was the same as Example 1 except that 0.1 part by weight of antibiotic (triclosan, Ciba) was mixed for 100 parts by weight of polybutylene terephthalate resin (1100, Toray) and the mixture was used as a yarn material.

As the result, a double tapered filament, which has an overall length of 16 mm, and is formed with a non-tapered area for tufting part with a length of 5 mm and taper parts with a length of 5.5 mm at two ends, was manufactured.

The taper part was inspected using a toolmaker's microscope (Olympus), and as the result, it was found that a diameter at 1 mm from an end point is 41% of a central diameter at half position of the filament, a diameter at 3 mm from the end point is 79% of the central diameter at half position of the filament and a diameter at 5.5 mm from the end point is 92% of the central diameter at half position of the filament.

Example 10

The same as Example 1 except that a monofilament with a diameter of 0.15 mm was manufactured by stretching to 6 times and a bundle has manufactured having a length of 23.1 mm (corresponding to 105% of a length of a 22 mm final product).

As the result, a double tapered filament, which has an overall length of 22 mm, and is formed with a non-tapered area for tufting part with a length of 11 mm and taper parts with a length of 5.5 mm at two ends, was manufactured.

The taper part was inspected using a toolmaker's microscope (Olympus), and as the result, it was found that a diameter at 1 mm from an end point is 39% of a central diameter at half position of the filament, a diameter at 3 mm from the end point is 77% of the central diameter at half position of the filament and a diameter at 5.5 mm from the end point is 92% of the central diameter at half position of the filament.

Comparative Example 1

Manufacture of a tapered filament was the same as Example 1 except that the melt closing process was not implemented.

That is, polybutylene terephthalate resin (Toraycon 1100, Toray) was put into an extruder and melt extruded at 250° C., followed by spinning using a nozzle with a size of 0.8 mm. The spun yarn was cooled with water and a monofilament with a diameter of 0.2 mm was then manufactured.

The stretched monofilaments were bundled and cut, thereby manufacturing a bundle having a diameter of 40 mm and a height of 18.4 mm (corresponding to 115% of a length of the final product).

An end of the manufactured bundle was dipped in a 35%, 110° C. aqueous sodium hydroxide solution for 180 minutes and then taken out. At that time, the dipping was implemented only to the portion that is placed at 4 mm from the end. However, white lump formed by hydrolysis of the resin was produced to the portion that is placed at 8 mm from the end by the capillary action.

Next, the opposite end was dipped in a 35%, 110° C. aqueous sodium hydroxide solution for 200 minutes and then taken out. At that time, the dipping was implemented only to the portion that is placed at 4 mm from the end. However, white lump formed by hydrolysis of the resin was produced to the portion that is placed at 6 mm from the end by the capillary action.

The white lumps produced in the two ends were cleaned two times and neutralized. As the result, the overall diameter of the filament was reduced, lengths of the left and right tapers were asymmetrically different and almost no non-tapered area for tufting part was formed, which made the tufting impossible.

Comparative Example 2

The same as Example 1, but a tapered filament with a diameter of 0.15 mm by implementing the stretch to 6.5 times with control of a discharge amount.

As the result, a double tapered filament, which has an overall length of 16 mm, and is formed with a non-tapered area for tufting part with a length of 5 mm and taper parts with a length of 5.5 mm at two ends, was manufactured.

The taper part was inspected using a toolmaker's microscope (Olympus), and as the result, it was found that a diameter at 1 mm from an end point is 33% of a central diameter at half position of the filament, a diameter at 3 mm from the end point is 65% of the central diameter at half position of the filament and a diameter at 5.5 mm from the end point is 77% of the central diameter at half position of the filament.

Although the diameter was controlled by control of the discharge amount in Comparative Example 2, white turbidity was generated due to high stretch ratio, durability was lowered and feeling of use was lowered due to high strength of the filament.

Comparative Example 3

The same as Example 1, but a double tapered filament with a diameter of 0.25 mm by implementing the stretch to 3.5 times with control of a discharge amount.

As the result, a double tapered filament, which has an overall length of 16 mm, and is formed with a non-tapered area for tufting part with a length of 5 mm and taper parts with a length of 5.5 mm at two ends, was manufactured.

The taper part was inspected using a toolmaker's microscope (Olympus), and as the result, it was found that a diameter at 1 mm from an end point is 52% of a central diameter at half position of the filament, a diameter at 3 mm from the end point is 91% of the central diameter at half position of the filament and a diameter at 5.5 mm from the end point is 98% of the central diameter at half position of the filament.

Although the diameter was controlled by control of the discharge amount in Comparative Example 3, strength of the filament was low due to low stretch ratio and thus the feeling of use was significantly lowered.

Comparative Example 4

The same as Example 1, but a double tapered filament, which has an overall length of 24 mm, and is formed with a non-tapered area for tufting part with a length of 14 mm and taper parts with a length of 5 mm at two ends, was manufactured.

The taper part was inspected using a toolmaker's microscope (Olympus), and as the result, it was found that a diameter at 1 mm from an end point is 21% of a central diameter at half position of the filament, a diameter at 3 mm from the end point is 32% of the central diameter at half position of the filament and a diameter at 5.5 mm from the end point is 49% of the central diameter at half position of the filament.

Comparative Example 5

The same as Example 1, but a double tapered filament, which has an overall length of 18 mm, and is formed with a non-tapered area for tufting part with a length of 2 mm and taper parts with a length of 8 mm at two ends, was manufactured by processing in a 25%, 110° C. sodium hydroxide for 180 minutes.

The taper part was inspected using a toolmaker's microscope (Olympus), and as the result, it was found that a diameter at 1 mm from an end point is 20% of a central diameter at half position of the filament, a diameter at 3 mm from the end point is 33% of the central diameter at half position of the filament and a diameter at 5.5 mm from the end point is 48% of the central diameter at half position of the filament.

Comparative Example 6

The same as Example 1, but a tapered filament, which has an overall length of 18 mm, and is formed with a non-tapered area for tufting part with a length of 3 mm and taper parts with a length of 7.5 mm at two ends, was manufactured by processing in a 35%, 150° C. sodium hydroxide for 180 minutes.

The taper part was inspected using a toolmaker's microscope (Olympus), and as the result, it was found that a diameter at 1 mm from an end point is 22% of a central diameter at half position of the filament, a diameter at 3 mm from the end point is 46% of the central diameter at half position of the filament and a diameter at 5.5 mm from the end point is 72% of the central diameter at half position of the filament.

The double tapered filaments manufactured in Examples and Comparative Examples were tufted into a power toothbrush, respectively, and then durability and feeling of use were measured through visual inspection.

Five-point measurement was implemented for 100 users, and average values are shown.

The durability was measured by whether bending of the filament occurred after the use of 20 times, and the feeling of use was evaluated totally for smoothness during the brushing, feeling of rubbing, feeling of cleaning and condition of gums.

The results are shown in Table 1 below.

TABLE 1

| | Durability | Feeling of use | Length tufted |
|---|---|---|---|
| Example 1 | 4.9 | 4.9 | 5 mm |
| Example 2 | 4.8 | 4.7 | 5 mm |
| Example 3 | 4.2 | 4.8 | 5 mm |
| Example 4 | 4.3 | 4.8 | 5 mm |
| Example 5 | 4.6 | 4.6 | 5 mm |
| Example 6 | 4.7 | 4.7 | 5 mm |
| Example 7 | 4.6 | 4.7 | 5 mm |
| Example 8 | 4.7 | 4.6 | 5 mm |
| Example 9 | 4.6 | 4.7 | 5 mm |
| Example 10 | 4.7 | 4.8 | 5 mm |
| Comparative Example 1 | Non-measurable | Non-measurable | Non-tuftable |
| Comparative Example 2 | 2.1 | 3.8 | 5 mm |
| Comparative Example 3 | 1.5 | 0.8 | 5 mm |
| Comparative Example 4 | 4.5 | 2.2 | 9 mm |
| Comparative Example 5 | Non-measurable | Non-measurable | Non-tuftable |
| Comparative Example 6 | Non-measurable | Non-measurable | Non-tuftable |

While the present invention has been described with respect to the specific embodiments, it will be apparent to those skilled in the art that various changes and modifications may be made without departing from the spirit and scope of the invention as defined in the following claims.

What is claimed is:

1. A method for manufacturing a double tapered filament for a power toothbrush, comprising: melt spinning a synthetic resin composition, processing stretched monofilaments into a bundle, cutting the bundle, melt closing an end of the bundle by heating the end to a melting temperature of the synthetic resin, dipping an opposite end in a processing bath containing an alkali solution until the opposite end is tapered, and dipping the melted end in a processing bath containing an alkali solution until the melted end is tapered.

2. The method of claim 1, wherein the method comprises:
a) melt spinning the synthetic resin composition and stretching the spun product to 4 to 6 times to manufacture a monofilament with a diameter of 0.1 to 0.25 mm;
b) processing the monofilament to a bundle with a diameter of 40 to 55 mm;
c) cutting the bundle to a length of 105 to 115% of a length of a final product;
d) heating an end of the bundle to the melting temperature of the synthetic resin to melt close the portion from the end of the bundle to 1 to 3 mm from the end of the bundle;
e) dipping an end opposite to the melted end in a processing bath containing an alkali solution at 100 to 140° C. and 30 to 60% concentration to taper the opposite end; and
f) dipping the melted end in a processing bath containing an alkali solution at 100 to 140° C. and 30 to 60% concentration to taper the melted end.

3. The method of claim 2, wherein the synthetic resin composition is a mixture of polyester resin and an additive.

4. The method of claim 3, wherein the polyester resin has a tensile strength of 250 to 2500 cN and an elongation of 15 to 30%.

5. The method of claim 2, wherein the dipping is implemented only to a point that is placed at 4 mm or less from the end point to form the taper part.

6. The method of claim 2, wherein in the tapered filament,
a diameter (D) is 0.1 mm≦D≦0.25 mm,
an overall length (L) is 16 mm≦L≦22 mm,
a length (Ls) of the non-tapered area for tufting part is 4 mm≦Ls≦12 mm, and
rest two ends except for the non-tapered area for tufting part form the taper parts.

7. The method of claim 2, wherein the tapering in the steps c) and 0 is implemented so that
a diameter at 0 to 1 mm from an end point is 0 to 45% of a central diameter at half position of the filament,
a diameter at 1 to 3 mm from the end point is 35 to 85% of the central diameter at half position of the filament, and
a diameter at 3 to 6 mm from the end point is 60 to 97% of the central diameter at half position of the filament.

* * * * *

UNITED STATES PATENT AND TRADEMARK OFFICE
CERTIFICATE OF CORRECTION

PATENT NO.        : 8,512,611 B2
APPLICATION NO.   : 12/870299
DATED             : August 20, 2013
INVENTOR(S)       : Yeon-Bok Kang Page 1 of 1

It is certified that error appears in the above-identified patent and that said Letters Patent is hereby corrected as shown below:

In the Claims

Column 13, Line 9, Claim 7, delete "0" and insert -- f) --

Signed and Sealed this
Fourteenth Day of January, 2014

Michelle K. Lee
*Deputy Director of the United States Patent and Trademark Office*